(12) United States Patent
Xiong et al.

(10) Patent No.: US 11,846,623 B1
(45) Date of Patent: Dec. 19, 2023

(54) CORE HOLDER AND PREDICTION METHOD FOR STARTING PRESSURE GRADIENT OF SHALE OIL BASED ON CORE HOLDER

(71) Applicant: Southwest Petroleum University, Chengdu (CN)

(72) Inventors: Yu Xiong, Chengdu (CN); MeiHua Chen, Fushun (CN); LingHong Wang, Kunming (CN); MeiJuan Guo, Xianyang (CN); HaiTao Hong, Chengdu (CN); MingQiu Li, Chengdu (CN); XiuQing Li, Chengdu (CN); Rui Zhang, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 18/336,966

(22) Filed: Jun. 17, 2023

(30) Foreign Application Priority Data

Aug. 29, 2022 (CN) .......................... 202211038875.1

(51) Int. Cl.
*G01N 33/24* (2006.01)

(52) U.S. Cl.
CPC .................................. *G01N 33/241* (2013.01)

(58) Field of Classification Search
CPC .................................................... G01N 33/241
See application file for complete search history.

(56) References Cited

U.S. PATENT DOCUMENTS

| 7,805,982 | B2 * | 10/2010 | Hilab ...................... E21B 49/02 |
| | | | 73/38 |
| 10,365,200 | B2 * | 7/2019 | Liu ........................ G01N 33/24 |
| 10,670,506 | B2 * | 6/2020 | Liu ........................ G01N 15/08 |
| 11,692,426 | B2 * | 7/2023 | Hou ........................ E21B 47/09 |
| | | | 166/250.01 |

(Continued)

FOREIGN PATENT DOCUMENTS

| CN | 104807958 A | 7/2015 |
| CN | 208223585 U | 12/2018 |

(Continued)

OTHER PUBLICATIONS

Gao Miaomiao et al., Calculation of Permeability Reservoir Rational Injection-Production Well Spacing by Introducing Start-up Pressure Gradient, Liaoning Chemical Industry, Dec. 2010, pp. 1276-1278, vol. 39, No. 12.

*Primary Examiner* — John Fitzgerald

(57) ABSTRACT

A core holder and a prediction method for starting pressure gradient of shale oil based on the core hold are provided. The core holder includes an inlet plug, an outlet plug, a core accommodating cavity disposed between the inlet plug and the outlet plug and used for accommodating the shale oil, a rubber gasket disposed between the outlet plug and the core accommodating cavity, and a microinjector including a microinjector needle portion that passes through the outlet plug and the rubber gasket in sequence to be in contact with the shale oil in the core accommodating cavity. The core holder and the method can solve problems that movable oil volume of a low-porosity, low-permeability and small-volume rock sample and a shale rock sample cannot be accurately measured, and that a movable scale and a starting pressure gradient of the shale oil cannot be measured.

8 Claims, 3 Drawing Sheets

(56) References Cited

U.S. PATENT DOCUMENTS

| | | | | |
|---|---|---|---|---|
| 2015/0354352 | A1* | 12/2015 | Ezzat | G01N 33/24 |
| | | | | 73/152.05 |
| 2020/0173975 | A1* | 6/2020 | Cinar | G01N 13/00 |
| 2021/0372280 | A1* | 12/2021 | Hou | E21B 43/168 |
| 2022/0082517 | A1* | 3/2022 | Song | G01N 33/241 |

FOREIGN PATENT DOCUMENTS

| | | | |
|---|---|---|---|
| CN | 109856033 B | * | 5/2020 |
| CN | 115389387 A | * | 11/2022 |

* cited by examiner

CORE HOLDER AND PREDICTION METHOD FOR STARTING PRESSURE GRADIENT OF SHALE OIL BASED ON CORE HOLDER

TECHNICAL FIELD

The disclosure relates to the field of unconventional oil reservoir development technology, and more particularly to a core holder and a prediction method for starting pressure gradient of shale oil based on the core holder.

BACKGROUND

As conventional oil and gas reservoirs have passed their development climax, focus of the oil and gas exploration worldwide has gradually shifted from the conventional oil and gas to unconventional oil and gas, and focus of global petroleum industry has also shifted to the unconventional oil and gas. However, exploration and development of shale oil are not as mature as that of shale gas. Scholars and petroleum workers in various countries have started to devote themselves to research on the shale oil, but most of them are at a level of geological resource mobility evaluation. Furthermore, there are fewer studies on the mobility of the shale oil at a development level, mainly because shale reservoir and seepage space is characterized by multi-genesis and multi-scale pore and seam coupling coexistence and the shale oil is characterized by high density, high viscosity, outstanding low fluidity, complex pore structure and low crude oil quality, resulting in various types of reservoir states, large differences and difficult flow, for the shale oil, and also resulting in difficult accurate establishment of experimental method for shale oil mobility.

At present, most experimental methods for the shale oil mobility also maintain at a conventional stage, such as a pyrolysis method, a nuclear magnetic method, a mercury injection method, a nitrogen adsorption method, etc., which cannot achieve accurate measurement of movable oil volume. Moreover, existing core holders are small in length change range and large in measurement errors, and can only meet the requirements of conventional rock core experiments. Therefore, the existing core holders cannot accurately measure the movable oil volume of small volume rock samples and shale rock samples with low porosity and low permeability, and cannot realize the measurement of movable scale conditions and starting pressure gradient of the shale oil.

SUMMARY

An objective of the disclosure is to provide a core holder and a prediction method for starting pressure gradient of shale oil based on the core holder, thereby solving problems that movable oil volume of a low-porosity, low-permeability and small-volume rock sample and a shale rock sample cannot be accurately measured and that a movable scale and a starting pressure gradient of the shale oil cannot be measured.

The technical solutions for solving the above technical problems are as follows.

The disclosure provides a core holder, which includes: an inlet plug, an outlet plug, and a core accommodating cavity. The core accommodating cavity is disposed between the inlet plug and the outlet plug and is used for accommodating the shale oil. The core holder further includes a rubber gasket disposed between the outlet plug and the core accommodating cavity, and a microinjector, which is provided with a microinjector needle portion. Furthermore, the microinjector needle portion is used to pass through the outlet plug and the rubber gasket in sequence to be in contact with the shale oil disposed in the core accommodating cavity.

In an embodiment, the microinjector further includes: a microinjector tube portion, and the microinjector tube portion is provided with a connection end connected to the microinjector needle portion; the outlet plug is provided with an entry end and an exit end, the entry end and the exit end are disposed opposite to each other along a length extension direction of the core holder, an end face of the entry end is provided with a groove, and the connection end is clamped in the groove.

In an embodiment, the connection end is sealed in the groove by a coating.

In an embodiment, the coating is a thermoset plastic epoxy resin coating.

In an embodiment, the rubber gasket is provided with a contact end face, the contact end face is close to the core accommodating cavity, the microinjector needle portion is provided with a needle tip, and a tip of the needle tip is flush with the contact end face.

In an embodiment, the inlet plug is a variable-length plug with an external thread.

In an embodiment, the core holder further includes an adjusting nut and a big nut, and the adjusting nut is disposed between the big nut and the inlet plug and is connected to the big nut and the inlet plug in a threaded connection manner.

In an embodiment, the microinjector is sleeved with a microinjector protective cover, and the microinjector protective cover is a visible organic safety cover.

The disclosure further provides a prediction method for starting pressure gradient of the shale oil based on the above-mentioned core holder, and the prediction method for starting pressure gradient of shale oil includes the following steps:

step 1, obtaining an oil volume of a shale oil sample under a preset condition by using the above-mentioned core holder;

step 2, calculating a starting pressure gradient according to the oil volume and physical data of the shale oil sample;

step 3, obtaining a first correlation index between a capillary pressure J function and a ratio K/φ between permeability and porosity;

step 4, obtaining a second correlation index between the starting pressure gradient and the ratio K/φ between permeability and porosity according to the starting pressure gradient, the first correlation index, and the ratio K/φ between permeability and porosity; and step 5, obtaining a predicted starting pressure gradient according to the second correlation index and an actual ratio K/φ between permeability and porosity;

In an embodiment, in the step 4, the second correlation index is calculated by the following formula:

$$\lambda = \alpha[(K/\varphi)^x]^{-n},$$

where $\lambda$ represents the starting pressure gradient, K/φ represents the ratio between permeability and porosity, $\alpha$ and $n$ represent regression coefficients, $x$ represents the first correlation index, and the second correlation index is $x \times (-n)$.

The disclosure has the following beneficial effects:

Under the condition that the geological conditions of the actual oil reservoir, the characteristics of the rock sample, the properties of crude oil and the experiment conditions are fully considered, the disclosure can achieve the shale movable conditions with different scales and the tests of shale movable oil volume while solving the problems that the conventional core holders cannot accurately measure the movable oil volume of shale reservoir cores. Compared with the core holders in the related art, the core holder of the disclosure is easy to operate, has higher experimental precision, and is more suitable for the movable oil experiments of unconventional oil reservoirs, especially the shale oil.

DESCRIPTION OF REFERENCE NUMERALS

1—inlet plug; 2—outlet plug; 21—groove; 22—entry end; 23—exit end; 3—core accommodating cavity; 4—rubber gasket; 41—contact end surface; 5—microinjector; 51—microinjector needle portion; 52—microinjector tube portion; 53—microinjector protective cover; 6—adjusting nut; 7—big nut; 8—cylinder.

DETAILED DESCRIPTION OF EMBODIMENTS

The principles and features of the disclosure will be described below with reference to attached drawings, which are merely used to explain the disclosure and are not intended to limit the scope of the disclosure.

Figure 1:
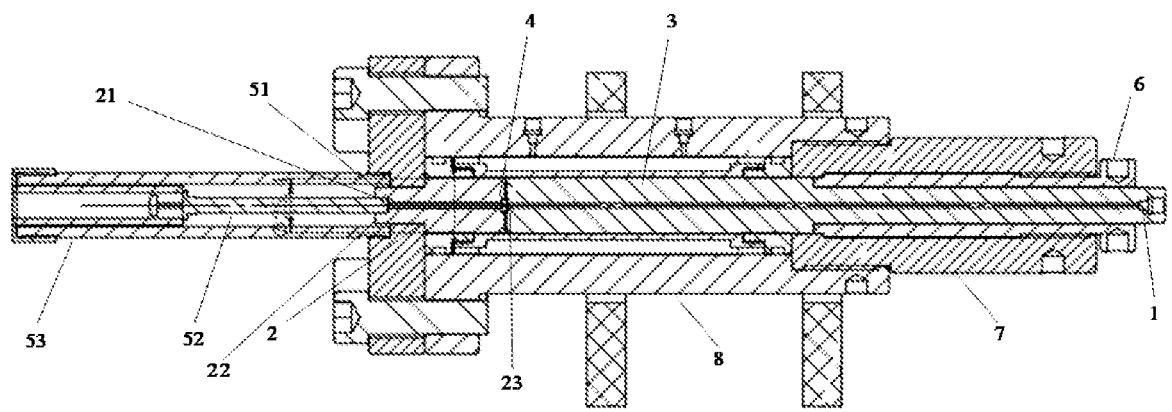
FIG. 1 illustrates a schematic structural diagram of a core holder according to an embodiment of the disclosure.
Figure 2:
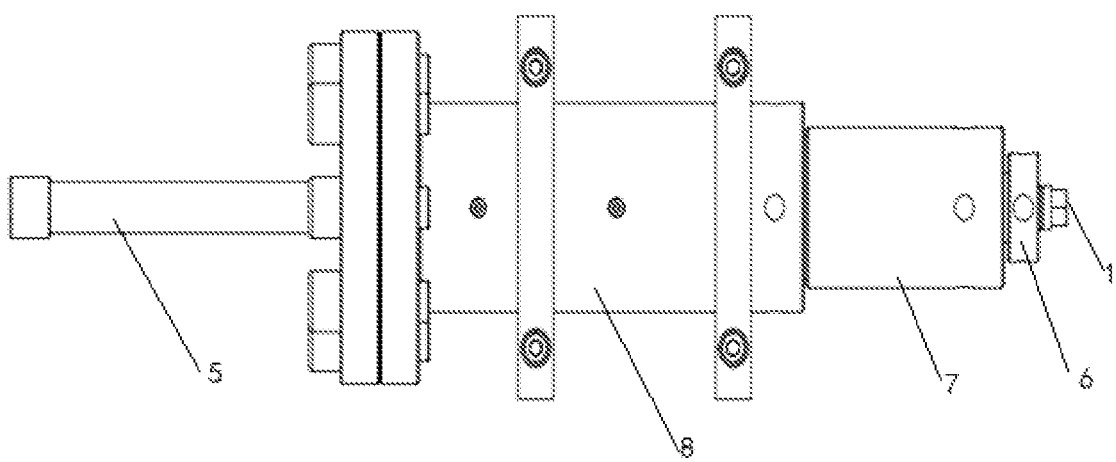
FIG. 2 illustrates a front view of the core holder according to an embodiment of the disclosure.
Figure 3:
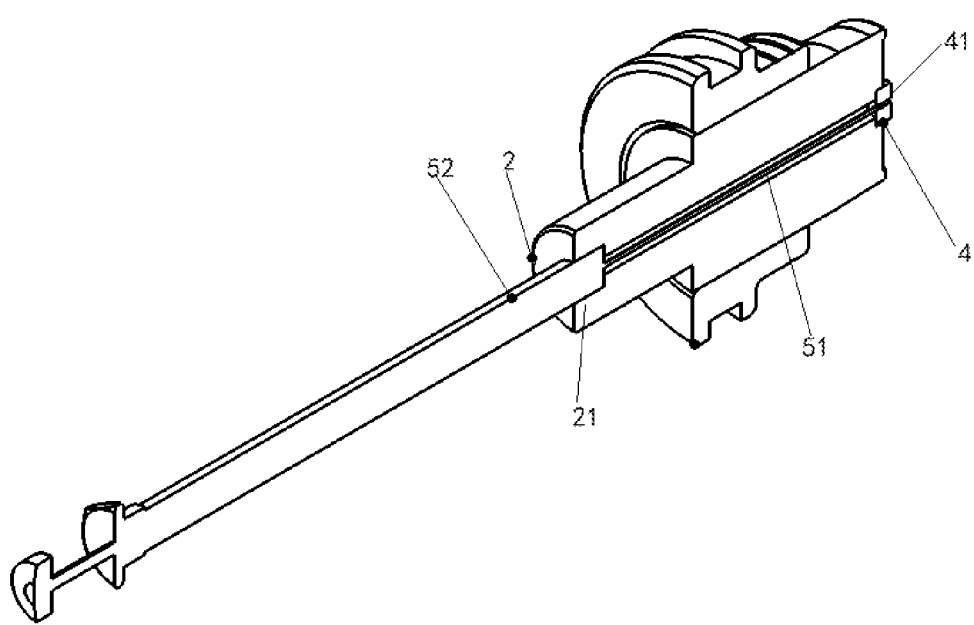
FIG. 3 illustrates a partial view of a connection between a microinjector and an outlet plug according to an embodiment of the disclosure.

The disclosure provides a core holder. As shown in FIGS. 1-3, the core holder of the disclosure includes: an inlet plug 1, an outlet plug 2, a core accommodating cavity 3 disposed between the inlet plug 1 and the outlet plug 2 and used for accommodating shale oil, a rubber gasket 4 disposed between the outlet plug 2 and the core accommodating cavity 3, and a microinjector 5 including a microinjector needle portion 51. The microinjector needle portion 51 is used to pass through the outlet plug 2 and the rubber gasket 4 in sequence to be in contact with the shale oil disposed in the core accommodating cavity 3.

In the disclosure, the microinjector 5 is a micro microinjector with a unit of microliter; and the rubber gasket 4 is a fluorine rubber gasket with a shape of cylindrical. Furthermore, the fluorine rubber gasket is resistant with high temperature, vacuum, high-pressure and corrosion.

Based on the characteristics of the rubber gasket, the microinjector needle portion 51 passes through the outlet plug 2 and the rubber gasket 4 in sequence, thereby make the microinjector 5 and the shale oil accommodated in the core accommodating cavity 3 connect seamlessly. Therefore, it can be ensured that oil driven by a rock core of the shale rock sample enters the microinjector 5 at the first time, which is a guarantee of the accurate measurement of the movable shale oil volume.

To fix the microinjector 5 and make the microinjector needle portion 51 pass through the outlet plug 2 and the rubber gasket 4 in sequence, the microinjector 5 further includes a microinjector tube portion 52, and the microinjector tube portion 52 is provided with a connection end connected to the microinjector needle portion 51. Furthermore, along a length extension direction of the core holder, the outlet plug 2 is provided with an entry end 22 and an exit end 23, the entry end 22 and the exit end 23 are disposed opposite to each other, an end face of the entry end 22 is provided with a groove 21, and the connection end is clamped in the groove 21, thereby realizing the fixation of the microinjector 5.

Considering the influence of a sealing manner on the accurate measurement, the connection end is sealed in the groove by a coating. In an illustrated embodiment, the coating is a thermoset plastic epoxy resin coating. However, those skilled in the related art may select other manners for the sealing, which is not specifically limited in the disclosure.

In order to prevent an exposed portion of the microinjector needle portion 51 in the core accommodating cavity 3 after that the microinjector needle portion 51 passes through the rubber gasket 4 from being damaged in a process of oil displacement, the rubber gasket 4 of the disclosure is provided with a contact end surface 41, the contact end surface 41 is an end surface close to the core accommodating cavity 3. Furthermore, the microinjector needle portion 51 is provided with a needle tip and a tip of the needle tip is flush with the contact end surface 41. In this way, it can be ensured that the service life of the microinjector 5 is prolonged while it is ensured that the oil driven by the core sample enters the microinjector 5 at a first time.

Under the condition of loading the shale rock sample in the core accommodating cavity 3, the shale rock sample occupies partial positions of the inlet plug 1, and then the inlet plug 1 extends into the core accommodating cavity 3, and therefore, the inlet plug 1 is designed to be a variable-length plug with an external thread. In this way, when the shale rock sample is loaded into the core accommodating cavity 3, the inlet plug 1 can still be tightened, thereby ensuring the sealing performance of the core holder.

To tighten the inlet plug 1, the core holder further includes an adjusting nut 6 and a big nut 7, the adjusting nut 6 is disposed between the big nut 7 and the inlet plug 1, and is connected to the big nut 7 and the inlet plug 1 respectively in a threaded connection manner. In this way, the adjusting nut 6 and the big nut 7 can rotate relative to their each other, and the adjusting nut 6 and the inlet plug 1 can also rotate relative to their each other, thereby achieving a variable-length adjustment.

Furthermore, to clearly observe scales on the microinjector tube portion 52 during operation, in an illustrated embodiment, the microinjector 5 is sleeved with a microinjector protective cover 53, and the microinjector protective cover 53 is a visible organic safety cover.

In addition, the core holder provided by the disclosure has a plurality of pressure measuring holes at its different positions in an axial direction of the core holder. The pressure measuring holes are used for realizing an aggregate control of confining pressure together with a pressure control system of a multifunctional oven. Pressure applied on the entry end 22 is controlled by a flow rate of a flat flow pump and is read out from a pressure gauge, and pressure applied on the exit end 23 is monitored and recorded by a computer pressure testing system through a high-precision pressure sensor.

Figure 4:
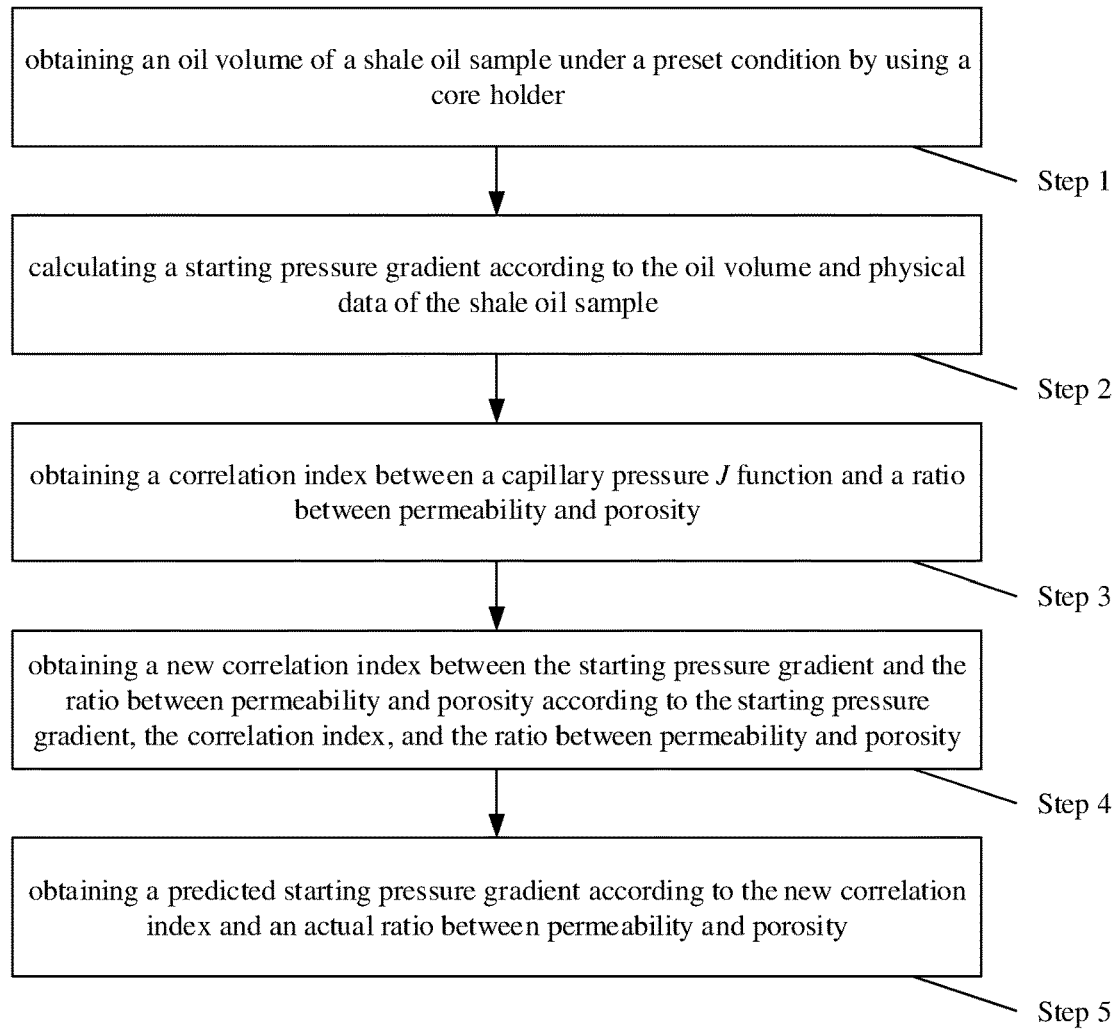
FIG. 4 illustrates a flowchart of a prediction method for starting pressure gradient of shale oil according to an embodiment of the disclosure.

As shown in FIG. 4, the disclosure also provides a prediction method for starting pressure gradient of the shale oil based on the core holder, and the method includes the following steps.

Step 1, an oil volume of a shale oil sample is obtained under a preset condition by using the core holder.

In the step 1, before acquiring the oil volume of the shale oil sample under the preset condition, the disclosure first performs the following operations:

A1, obtaining a length, a diameter and initial weight data of a shale sample after washing oil, and drying treatments;

preset, thereafter, to perform an oil displacement experiment. The displaced oil volume in the microinjector tube portion 52 under different pressure differences is observed, the movable condition of the shale oil sample is quantitatively analyzed, and the pressure gradient of the shale oil sample is calculated in combination with the physical data of the shale oil sample.

Experimental data of the displacement movable oil ratio of YT1-9 fine sandstone on Lianggaosahn Mem (also referred to Lianggaoshan Mem) are as follows. Under the room temperature and the pressure gradient of 0.600 MPa per centimeter (MPa/cm), the displaced shale oil volume from the shale sample is 0.126 milligrams per gram (mg/g), and the movable oil ratio is 7.84%.

TABLE 1 illustrates the experimental data of the pressure gradient of the shale sample and the movable shale oil volume.

| Number | Rock character | Length/ cm | Porosity/ % | Permeability/ mD | Entry end pressure/ MPa | Exit end pressure/ MPa | Saturated oil volume/g | Movable oil volume/g | Proportion of movable oil/% |
|---|---|---|---|---|---|---|---|---|---|
| YT1-9 | Fine sandstone | 4.798 | 2.54 | 0.0657 | 2.98 | 0.101 | 0.102 | 0.008 | 7.84 |

A2, obtaining a volume and a density of the shale sample according to the length, the diameter and the weight data of the shale sample;

A3, vacuumizing the shale sample for 24 hours by using a core vacuumizing and pressurizing saturation device at room temperature and then, performing sustained compression saturation for 72 hours at 12 mega Pascal (MPa) to obtain a saturated shale sample, and soaking the saturated shale sample in crude oil all the time to obtain a composition composed of the saturated shale sample and the crude oil;

A4, obtaining a saturation weight of the saturated shale sample; and

A5, placing the composition in the core accommodating cavity 3 from an entry end 22 of the core holder, slowly pushing out the composition until an end face of the rock core of the composition is flush with an exit end 23 of the core holder, then pushing the outlet plug 2 assembled with the rubber gasket 4 against the end face of the rock core of the composition until an end face of the outlet plug 2 is flush with an end face of a cylinder 8 of the core holder, tightening screw threads disposed on the exit end 23 of the outlet plug 2 according to diagonal order, and then loading the microinjector 5 in the outlet plug 2, further sealing periphery of the outlet plug 2 with the epoxy resin coating, then installing the microinjector protective cover 53 outside the microinjector 5, and finally tightening the inlet plug 1 disposed on the exit end 23 of the core holder.

Step 2: a starting pressure gradient according to the oil volume and the physical data of the shale oil sample is calculated.

The installed core holder is placed in the oven (also referred to the multifunctional oven), the pressure sensor and the flat flow pump are connected, and a power supply of the oven is opened. At the same time, the pressure applied on the entry end 22, the confining pressure and the temperature are preset.

Step 3: a correlation index (also referred to a first correlation index) between a capillary pressure J function and a ratio $K/\varphi$ between permeability and porosity is obtained.

Figure 5:
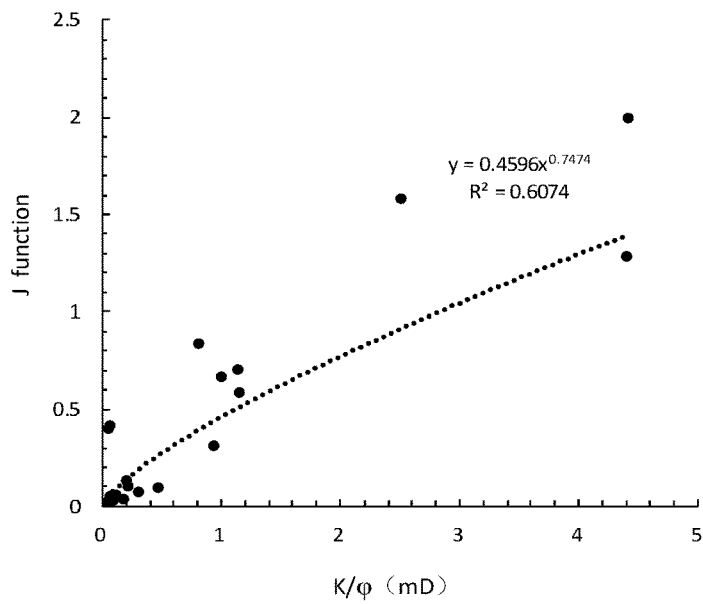
FIG. 5 illustrates a schematic diagram of a correlation index between a capillary pressure J function and a ratio K/φ between permeability and porosity.

As shown in FIG. 5, the correlation index between the capillary pressure J function and the ratio $K/\varphi$ between permeability and porosity is 0.7474 by fitting the experimental results of the core holder provided by the disclosure, and $R^2$ (referred to a variance) is 0.6074.

Step 4, a new correlation index (also referred to a second correlation index) between the starting pressure gradient and the ratio $K/\varphi$ between permeability and porosity is obtained according to the starting pressure gradient, the first correlation index, and the ratio $K/\varphi$ between permeability and porosity.

Figure 6:
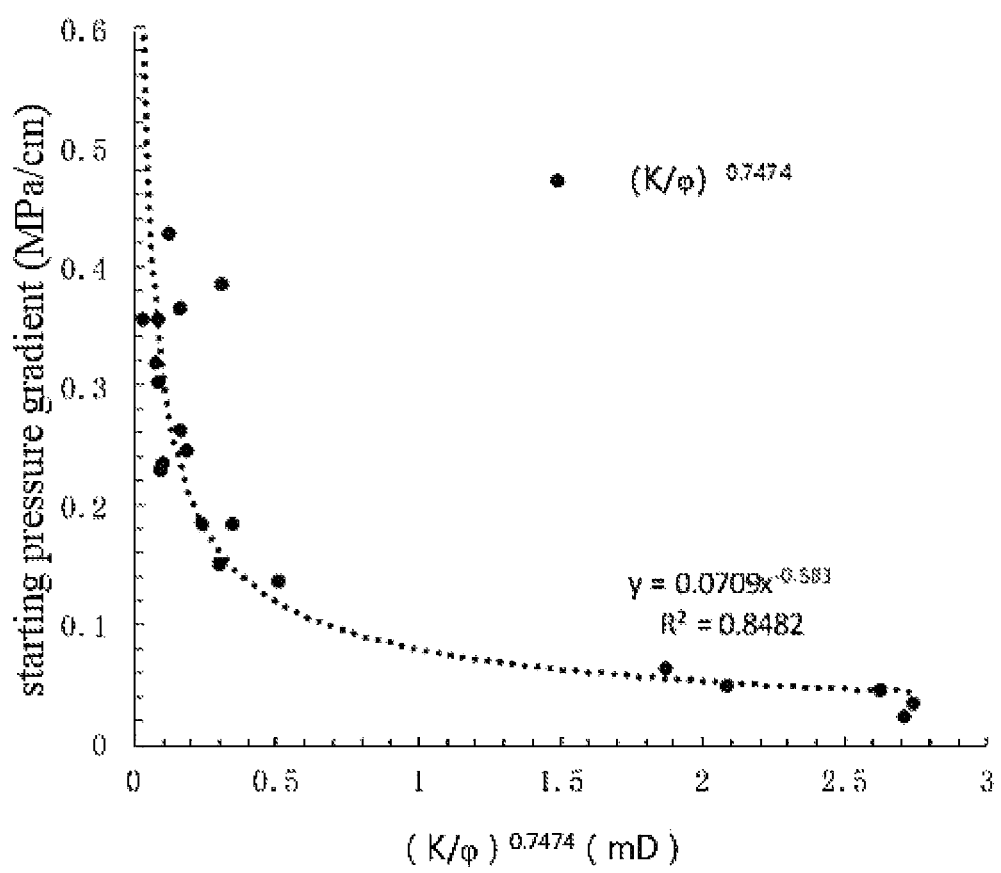
FIG. 6 illustrates a schematic diagram of a correlation index between an experimental pressure gradient and $(K/\varphi)^{0.7474}$.

The correlation index 0.7474 is substituted into the calculation in the step 4, and the new correlation index is calculated by using the following formula:

$$\lambda = \alpha[(K/\varphi)^x]^{-n},$$

where $\lambda$ represents the starting pressure gradient, $K/\varphi$ represents the ratio between permeability and porosity, a and n represent regression coefficients, x represents the correlation index, and the second correlation index is x×(−n). In an illustrated embodiment, x is 0.7474. As shown in FIG. 6, the new correlation index is equal to 0.7474×(−0.583), and a new $R^2$ is equal to 0.8482, and in fact, the $R^2$ is closer to 1, the correlation is better. Therefore, the calculation method is more suitable for the calculation of the starting pressure gradient of the shale oil.

Step 5, a predicted starting pressure gradient is obtained according to the new correlation index and an actual ratio $K/\varphi$ between permeability and porosity.

According to a method for predicting the starting pressure gradient of average permeability in reservoirs, the starting pressure gradient of the experimental core sample is obtained 0.564 MPa/cm. The starting pressure gradient obtained by the prediction method of the disclosure after introducing the J function is 0.597 MPa/cm, and the actual starting pressure gradient obtained based on the core holder of the disclosure is tested to obtain 0.600 MPa/cm. Therefore, the error of the prediction method of the disclosure is only 0.5%, which illustrates that the calculation precision is obviously improved, thereby verifying the correctness of the disclosure.

The foregoing is merely the illustrated embodiment of the disclosure and is not intended to limit the disclosure, and any modifications, equivalent substitutions, improvements, etc. made within the spirit and principle of the disclosure shall fall within the protection scope of the disclosure.

What is claimed is:

1. A prediction method for starting pressure gradient of shale oil based on a core holder, wherein the core holder comprises:
   an inlet plug;
   an outlet plug;
   a core accommodating cavity, disposed between the inlet plug and the outlet plug and configured to accommodate a shale oil sample;
   a rubber gasket, disposed between the outlet plug and the core accommodating cavity; and
   a microinjector, wherein the microinjector comprises: a microinjector needle portion, the microinjector needle portion is configured to pass through the outlet plug and the rubber gasket in sequence to be in contact with the shale oil sample accommodated in the core accommodating cavity;
   wherein the prediction method for starting pressure gradient of shale oil comprises:
   step 1, obtaining an oil volume of the shale oil sample under a preset condition by using the core holder;
   step 2, calculating a starting pressure gradient according to the oil volume and physical data of the shale oil sample;
   step 3, obtaining a first correlation index between a capillary pressure J function and a ratio $K/\varphi$ between permeability and porosity, wherein K represents the permeability, and $\varphi$ represents the porosity;
   step 4, obtaining a second correlation index between the starting pressure gradient and the ratio $K/\varphi$ between permeability and porosity according to the starting pressure gradient, the first correlation index, and the ratio $K/\varphi$ between permeability and porosity; and
   step 5, obtaining a predicted starting pressure gradient according to the second correlation index and an actual ratio $K/\varphi$ between permeability and porosity;
   wherein in the step 4, the second correlation index is calculated by the following formula:

$$\lambda = \alpha [(K/\varphi)^x]^{-n}$$

where $\lambda$ represents the starting pressure gradient, $K/\varphi$ represents the ratio between permeability and porosity, $\alpha$ and n represent regression coefficients, x represents the first correlation index, and the second correlation index is x×(−n).

2. The prediction method for starting pressure gradient of the shale oil based on the core holder according to claim 1, wherein the rubber gasket is provided with a contact end face, the contact end face is close to the core accommodating cavity, the microinjector needle portion is provided with a needle tip, and a tip of the needle tip is flush with the contact end face.

3. The prediction method for starting pressure gradient of the shale oil based on the core holder according to claim 1, wherein the microinjector is sleeved with a microinjector protective cover, and the microinjector protective cover is a visible organic safety cover.

4. The prediction method for starting pressure gradient of the shale oil based on the core holder according to claim 1, wherein the inlet plug is a variable-length plug with an external thread.

5. The prediction method for starting pressure gradient of the shale oil based on the core holder according to claim 4, wherein the core holder further comprises: an adjusting nut and a big nut, and the adjusting nut is disposed between the big nut and the inlet plug and is connected to the big nut and the inlet plug in a threaded connection manner.

6. The prediction method for starting pressure gradient of the shale oil based on the core holder according to claim 1, wherein the microinjector further comprises: a microinjector tube portion, the microinjector tube portion is provided with a connection end connected to the microinjector needle portion; the outlet plug is provided with an entry end and an exit end, the entry end and the exit end are disposed opposite to each other along a length extension direction of the core holder, an end face of the entry end is provided with a groove, and the connection end is clamped in the groove.

7. The prediction method for starting pressure gradient of the shale oil based on the core holder according to claim 6, wherein the connection end is sealed in the groove by a coating.

8. The prediction method for starting pressure gradient of the shale oil based on the core holder according to claim 7, wherein the coating is a thermoset plastic epoxy resin coating.

* * * * *